United States Patent [19]

Bryant et al.

[11] 4,377,638

[45] Mar. 22, 1983

[54] MICROBIOLOGICAL PRODUCTION OF LOWER ALIPHATIC CARBOXYLIC ACIDS

[75] Inventors: Marvin P. Bryant; Barbara R. S. Genthner, both of Urbana, Ill.

[73] Assignee: University Patents, Inc., Norwalk, Conn.

[21] Appl. No.: 278,678

[22] Filed: Jun. 29, 1981

[51] Int. Cl.³ .................................................. C12P 7/40
[52] U.S. Cl. .................................. 435/136; 435/140; 435/141
[58] Field of Search ........................ 435/136, 140, 141

[56] References Cited

U.S. PATENT DOCUMENTS

| | | | |
|---|---|---|---|
| 1,625,732 | 4/1927 | LeFranc | 435/140 X |
| 1,913,346 | 6/1933 | Stiles | 435/140 X |
| 1,932,755 | 10/1933 | Stiles et al. | 435/140 X |
| 2,549,765 | 4/1951 | Beesch et al. | 435/140 |
| 2,997,424 | 8/1961 | Mayer | 435/140 |
| 3,779,868 | 12/1973 | Hikolaev et al. | 435/140 |
| 4,282,323 | 8/1981 | Yates | 435/140 |

FOREIGN PATENT DOCUMENTS

572664 10/1945 United Kingdom ............... 435/140

*Primary Examiner*—Robert A. Yoncoski
*Attorney, Agent, or Firm*—George M. Yahwak

[57] ABSTRACT

Lower aliphatic carboxylic acids of from 1 to 6 carbon atoms or salts thereof are prepared by culturing the microorganism *Eubacterium limosum* in a nutrient medium containing at least one member of the group consisting of carbon monoxide and a mixture of hydrogen and carbon oxide under substantially anaerobic conditions.

12 Claims, 6 Drawing Figures

MICROBIOLOGICAL PRODUCTION OF LOWER ALIPHATIC CARBOXYLIC ACIDS

BACKGROUND OF THE INVENTION

This invention relates to the field of microbiological processes and, more particularly, to the microbial production of lower aliphatic carboxylic acids.

At the present time when worldwide demand for organic chemicals is at an all-time high but the usual sources for many of such products, i.e., petroleum and natural gas, are in everdwindling supply, considerable interest has been directed to other forms of carbon such as biomass, coal and shale as raw material for industrial organic syntheses. Many fermentations utilizing carbohydrate substrates have been proposed or developed for obtaining organic materials. While ethanol fermentation is especially notable in this regard, other organics, notably the lower aliphatic carboxylic acids such as acetic, propanoic and butyric acid, have been successfully obtained as products of microbial metabolism. U.S. Pat. No. 1,371,611 describes a process for obtaining formic, acetic and butyric acids by the microbial fermentation of marine algae or sea-weed, presumably, the carbohydrate matter therein. U.S. Pat. No. 1,625,732 describes a process for producing butyric acid from the fermentation of hydrolyzed cellulose employing garden soil bacilli as the fermenting organism. Lactic and acetic acids are obtained from the fermentation of hexoses and pentoses by a microorganism whose characteristics are described in U.S. Pat. No. 1,856,425. Acetic, propionic and butyric acids or salts of organic acids are prepared by the fermentation of carbohydrates employing *Bacterium acidi propionici*, an organism isolated from Swiss cheese, as described in U.S. Pat. No. 1,913,346. Butyric acid is obtained in the process of U.S. Pat. No. 1,951,250 by the action of butyric acid bacteria on distillers' slop. Lower aliphatic acids, in particular, acetic, propionic and butyric acids, are obtained by fermenting a carbohydrate mash with the bacterium whose characteristics are described in U.S. Pat. No. 2,549,765. Dewatered human waste is metabolically utilized by a microorganism from the genus of Butyribacterium under anaerobic conditions to produce carboxylic acids which are thereafter decarboxylated to hydrocarbons in accordance with the process decribed in U.S. Pat. No. 3,962,035.

Coal, too, has been extensively studied as a raw material source for organic chemicals due to its abundance in many regions of the world, particularly in the United States where it is estimated to constitute 69% of the total estimated recoverable resources of fossil fuel whereas petroleum and natural gas are only about 7%. Many proposals for utilizing coal as a feed source for the manufacture of a variety of organic chemicals are initially based upon the partial oxidation of coal to provide a gaseous mixture predominantly made up of carbon monoxide and hydrogen, e.g., so-called "synthesis gas" or "syngas". Recent developments have led to a variety of catalyzed reactions involving the conversion of syngas to alkanols, glycols, carboxylic acids, esters, aldehydes, ethers, etc. Thus, for example, syngas has been catalytically converted to methanol in accordance with the reaction:

$$CO + 2H_2 \rightarrow CH_3OH$$

It has previously been recognized that a strain of *Eubacterium limosum* (synonomous with *Butyribacterium rettgeri*) can utilize methanol to provide acetic acid (Hamlett, et al., *Bacteriol. Proceed. Amer. Soc. Mirobiol.*, p. 149 (1969)). However, it has not been previously known or recognized that *Eubacterium limosum* (ATCC 8486) can convert carbon monoxide or a mixture of hydrogen and carbon oxide as, for example, obtained from the gasification of coal, to lower aliphatic carboxylic acids and/or corresponding salts.

SUMMARY OF THE INVENTION

It has now been surprisingly discovered that *Eubacterium limosum* can utilize gaseous carbon monoxide or a mixture of hydrogen and carbon oxide under anaerobic conditions to provide significant quantities of a lower aliphatic carboxylic acid containing up to six carbon atoms or mixture and/or salt thereof. This discovery is believed to have considerable significance for the organic chemical industry considering the high level of interest in exploiting non-traditional raw materials as discussed above.

The invention herein is particularly adapted to the production of acetic acid, valeric acid, butyric acid or caproic acid, mixtures thereof and/or the salts thereof, especially the alkali metal salts such as the sodium and potassium salts and the alkaline earth metal salts such as the calcium and magnesium salts.

DESCRIPTION OF THE PREFERRED EMBODIMENTS

A. CULTURING PROCEDURES

A. Substrates

While economic considerations make syngas a preferred substrate herein, any other source for a mixture of a carbon oxide and hydrogen can be used herein with equally good results.

A typical purified syngas will have the composition, on a water-free basis, in volume percentages, as follows: hydrogen, 51; carbon monoxide, 40; carbon dioxide, 4; methane, 1; and nitrogen, 4.

Syngas can be prepared from fossil fuels by any of the known methods, including such *in situ* gasification processes as the underground partial combustion of coal and petroleum deposits. The term fossil fuels as used herein is intended to include anthracite and bituminous coal, lignite, crude petroleum, shale oil, oil from tar sands, natural gas, as well as fuels derived from simple physical separations or more profound transformations of these materials, including coked coal, petroleum coke, gas oil, residua from petroleum distillation, and two or more of any of the foregoing materials in combination. Other carbonaceous fuels such as peat, wood and cellulosic waste materials can also be used.

Although various processes can be employed for the gasification, those of major importance depend either on the partial combustion of the fuel with an oxygen-containing gas or on the high temperature reaction of the fuel with steam, or on a combination of these two reactions. An excellent summary of the art of gas manufacture, including syngas, from solid and liquid fuels, is given in the *Encyclopedia of Chemical Technology*, Edited by Kirk-Othmer, Second Edition, Volume 10, pages 353–433, (1966), Interscience Publishers, New York, NY, the contents of which are incorporated by reference herein. The techniques for gasification of coal or other solid, liquid or gaseous fuel are not considered to be per se inventive here.

The raw synthesis gas produced from fossil fuels will contain various impurities such as particulates, sulfur compounds and metal carbonyl compounds, and will be characterized by a hydrogen-to-carbon oxides ratio which will depend on the fossil fuel and the particular gasification technology utilized. In general, it is desirable for the efficiency of the subsequent microbiological conversion step to purify the raw synthesis gas by the removal of impurities. Techniques for such purification are known and are not part of this invention.

The volume ratio of hydrogen to carbon oxide is not critical and can vary widely with ratios of from about 0.2:1 to about 10:1, and especially from about 0.4 to about 5:1, being entirely suitable. If desired, the amount of hydrogen present in syngas can be increased (at the expense of carbon monoxide therein) by catalytically reacting carbon monoxide with steam to provide a mixture of carbon dioxide and hydrogen, i.e., the so-called water gas shift reaction. Thus, it is within the scope of this invention to employ carbon monoxide alone, a gaseous mixture of hydrogen and carbon monoxide, hydrogen and carbon dioxide or hydrogen, carbon monoxide and carbon dioxide as substrates for conversion to lower aliphatic carboxylic acids/salts.

B. Strains of *Eubacterium limosum*

Strains RF (ATCC 31914) and S (ATCC 31915) of *Eubacterium limosum* were isolated from the rumen of a sheep fed a molasses-based diet, and the effluent of the primary anaerobic sewage sludge digestor in Urbana, Illinois, respectively. The daily diet of the sheep contained 1 kg of a molasses mixture, 0.08 kg soybean oil meal (40% crude protein) and 0.1 kg wheat straw. The molasses mixture contained 41.3 kg black strap molasses, 1.36 kg urea, 0.23 kg trace mineral salts, 0.34 kg dicalcium phosphate, 0.23 kg NaCl, and 1.0 kg water. Strain ATCC 8486 was obtained from the Anaerobe Laboratory, Virginia Polytechnic Institute and State University (VPI) Blackburg, Virginia and strain L34 was a lactate-fermenting strain isolated from the rumen of a young calf (Bryant, et al., *J. Dairy Sci.* 41:1747–1767 (1958)) and subsequently identified as a strain of *Eubacterium limosum*.

C. Anaerobic Culturing Procedures and Media

Employing a gaseous mixture of 80% $H_2$—20% $CO_2$ by volume, the *Eubacterium limosum* strains were cultured in tubes pressurized to two atmospheres and incubated on a shaker substantially in accordance with the procedures described by Balch, W. E., et al., *Appl. Environ. Microbiol.*, 32:781–791 (1976) which is incorporated by reference herein. Similar procedures were used to cultivate the *Eubacterium limosum* strains in the presence of carbon monoxide and a mixture of $H_2$—CO.

The basal medium contained 5% rumen fluid, B-vitamins, minerals, $NaHCO_3$, cysteine-$Na_2S$ reducing solution, and an 80% $N_2$—20% $CO_2$ gas phase having a final pH of 7.2. The medium was prepared as previously described in McInerney, et al., *Arch. Microbiol.*, 122:129–135 (1979) which is incorporated by reference herein, except that 10 mg $Na_2SeO_3$ was added to the trace mineral solution and the vitamin solution contained (per liter) 20 mg each of biotin and folic acid; 10 mg pyridoxal-HCl; 60 mg lipoic acid; and 50 mg each of riboflavin, thiamine-HCl, Ca-D-pantothenate, cyanocobalamin, p-aminobenzoic acid, and nicotinic acid. The chemically defined medium was the same as the basal medium, except the rumen fluid was replaced by sodium acetate-$3H_2O$ (0.2 or 0.3%). The anaerobic dilution solution had the same composition as the basal medium except the rumen fluid and vitamin solution were deleted.

Methanol was placed in sterile rubber-stoppered tubes and shaken vigorously after flushing under the $N_2$—$CO_2$ gas phase (3 times) before adding it to the cooled, sterile medium.

Incubations were at 35° C. unless otherwise indicated.

Pure cultures were maintained in stabbed slants in 13×100 mm tubes containing 3.5 ml of basal medium with 0.2% methanol and 1.0% Bacto agar (Difco) added. They were incubated until growth occurred and stored at 4° C. until needed.

Oxygen sensitivity was determined in methanol stab slants substantially as described by Bryant, et al., *J. Dairy Sci.*, 36:205–217 (1953) which is incorporated by reference herein, and by inoculating a glucose (0.3%) medium similar to the basal medium, except that it was prepared aerobically with a potassium phosphate buffer (0.05 M; pH 7.4).

D. Most Probable Numbers (MPN) of Methanol-utilizing Bacteria

A one-liter sample of anaerobic digestor sludge was collected for MPN determination in a one-liter Erlenmeyer flask with a one-way gas valve. Similar 500 ml samples of rumen fluid were collected seven hours after feeding from two fistulated sheep on the molasses-based diet and from a fistulated steer on a 70% hay-30% grain mixture diet. The rumen fluid samples were collected with a perforated pipe attached to a vacuum flask and hand pump. The samples were gassed with 80% $N_2$—20% $CO_2$ and mixed well before using.

Samples were diluted in 10-fold serial dilutions in 18×150 mm tubes containing 9.0 ml of anaerobic dilution solution. One ml aliquots of the diluted sample, containing between 1 µliter and 1 pliter of the original rumen fluid, were inoculated into triplicate 18×150 mm tubes containing 6 ml of the basal medium with 0.3% (v/v) methanol and 0.1% (w/v) sodium acetate-$3H_2O$ (enrichment medium). Growth was estimated daily by optical density (OD) for 11 days, except in the case of the steer samples which were monitored for 30 days. The gas phase of the cultures were then analyzed by the method of McInerney, et al., *Arch. Microbiol.*, 122:129–135 (1979), supra. The MPN was estimated from the number of tubes showing increased growth compared to control cultures without methanol as described by Rodina, A. G., *Methods in Aquatic Microbiology*, pp. 177–180, Balt., Md., University Park Press (1972) which is incorporated by reference herein.

E. Isolation of Methanol-utilizing *Eubacterium limosum*.

Those MPN cultures which contained the least amount of inoculum but indicated growth on methanol were diluted with anaerobic dilution solution and 0.5 ml of the appropriate dilution was used to inoculate roll tubes (18×150 mm) containing 7 ml of the same MPN medium to which 2% (w/v) Bacto agar (Difco) was added. After incubation, well-isolated colonies were picked and stabbed into methanol slants with the same composition as the medium used for the maintenance of strains employing substantially the same techniques described by Bryant, M. P., *Am. J. Clin. Nutr.*, 25:1324–1328 (1972) which is incorporated by reference herein.

F. Morphology

Morphology, motility and culture purity were determined by examining wet mounts, which were made from the water of syneresis of methanol slant cultures, under the phase contrast microscope. Gram-stained preparations were also examined.

G. Temperature of Growth

Temperature range and optimum temperature for growth (OD) on methanol was determined for the temperatures from 10° to 49° C. at intervals of 2°-3° C. Triplicate 18×150 mm tubes containing 10 ml of basal medium with 0.3% (v/v) methanol were inoculated and incubated at each temperature.

H. Heat resistance and Spore-formation

Heat resistance and spore formation were determined in 10-day and month-old cultures grown in the basal medium with 0.3% (v/v) methanol and in month-old cultures grown in the sporulation medium described by Duncan, C. L., et al., *Appln. Microbial.* 16:82–89 (1968) which is incorporated by reference herein. Triplicate tubes (13/100 mm) of the methanol medium were inoculated with 0.1 ml of the cultures herewith. The tubes were heated in a water bath to 70° C. and held at this temperature for 10 minutes. A second set of tubes were heated to 80° C. and held for 15 minutes. Tubes were quickly cooled to an ice bath and incubated. Growth was monitored for two weeks. Detection of spores was attempted with the above cultures by examining wet mounts with the phase-contrast microscope as well as smears of the cultures stained by the method described by Norris, et al. in *Methods in Microbiology*, pp. 105–134, New York, Academic Press, Inc. Vol. 5A which is incorporated by reference herein.

I. Utilization of Substrate

Utilization of substrate was determined in the basal medium (13×100 mm tubes; 3.5 ml medium) containing 20 mM of the compound to be tested. Controls included uninoculated tubes of each medium and inoculated tubes of medium without an energy source. Duplicate tubes were inoculated and growth (OD) was monitored until maximum growth occurred.

J. Growth on 80% $H_2$—20% $CO_2$

The basal medium was used for growth on 80% $H_2$—20% $CO_2$ by volume, except the sodium bicarbonate component therein was doubled. Five ml amounts were placed in serum capped tubes (18×150 mm), autoclaved, and stored under a 60% $N_2$—40% $CO_2$ gas phase at atmospheric pressure. Tubes were inoculated via syringe with 0.1 ml of culture. After inoculation the gas phase was changed to 80% $H_2$—20% $CO_2$ at two atmospheres of pressure as in Balch, W. E., et al., *Appl. Environ. Microbiol.*, 40:626–632 (1980), supra. Cultures were maintained on $H_2$—$CO_2$ by weekly transfers of 0.1 ml of culture and were repressurized daily.

K. Growth on CO

The same media employed in J., supra, was used to propagate growth in the presence of substantially pure CO.

L. Growth on $H_2$—CO

The same media employed in J., supra, was used to propagate growth in the presence of a mixture of $H_2$—CO.

M. Nutrients

The utilization of acetate anion for promoting growth on a number of substrates was determined by comparing growth in the basal medium supplemented with the substrate with and without rumen fluid and with sodium acetate—$3H_2O$ (0.3%) replacing the rumen fluid (chemically defined medium). Acetate utilization during growth on $H_2$—$CO_2$ was determined in an $H_2$—$CO_2$ medium lacking rumen fluid (chemically defined) with inocula which had been washed three times in anaerobic dilution solution.

Vitamin requirements for growth were investigated by deleting single vitamins, or both folic acid and p-aminobenzoic acid, from the chemically defined 0.2% methanol medium containing 0.2% sodium acetate—$3H_2O$. Vitamins which affected growth during the single deletion experiment were added to the chemically defined methanol, or $H_2$—$CO_2$, medium in various combinations at the concentrations described for the basal medium with no other vitamins present. Cultures were serially passed through these minimal vitamin media five times.

Nitrogen sources were studied using a chemically defined methanol medium containing 1.0 mM $NH_4Cl$ supplemented with 2.0 mM of a nitrogen compound to be studied. Growth (OD) was monitored until maximum growth was obtained or for one week if growth did not occur. All nitrogen compounds were added to the medium before autoclaving except urea, biuret and allantoin, which were filter sterilized before adding to sterile medium.

Casein, gelatin and esculin hydrolysis were investigated using the procedures described in the *Anaerobe Laboratory Manual* (VPI) which is incorporated by reference herein, except that the media used contained the vitamin and mineral solutions described for the basal medium and were buffered with sodium bicarbonate and an 80% $N_2$—20% $CO_2$ gas phase to a pH of 7.2. Triplicate tubes were inoculated and tested for hydrolysis.

II. ANALYTICAL PROCEDURES

Growth on $H_2$—$CO_2$ was determined by measuring the optical density (OD) at 600 nm in 18×150 mm tubes with a Bausch and Lomb Spectronic 70. Generation times were calculated and gas analysis was done as previously described by McInerney, et al., supra.

Volatile aliphatic carboxylic acids in the culture supernatant were determined as described by Salanitro, et al., *Appl. Microbio.*, 29:374–381 (1975) which is incorporated by reference herein or by acidification to free aliphatic carboxylic acids in which 0.2 ml 30% phosphoric acid was added to 1.8 ml of culture supernatant in acid-cleaned 13×100 mm screw cap tubes. 0.2 ml of the acidified samples was transferred to conical chromatograph vials and sealed with a serum cap. Free aliphatic carboxylic acids and methanol were analyzed using an SP-1000 column (10% SP1000, 1% $H_3PO_4$, 100/120 Chromosorb W, 6 ft; Supelco, Inc., Bellefonte, Penn.) at 150° C. and 80° C., respectively, in a Hewlett Packard 5830A Gas Chromatograph with a hydrogen-flame detector and 18850A GC terminal. Ammonia was determined using the method described by Chaney, et al., *Clin. Chem.*, 8:130–132 (1962) which is incorporated by reference herein.

To determine the % quanine plus cytosine (% G+C) of the DNA, a 3% inoculum was added to a serum-stoppered bottle containing 2 liters of basal medium with 0.3% methanol (v/v). Cells were harvested during logarithmic growth by centrifuging at 10,400×g for 20 min. DNA was isolated and purified by the method of Marmur in *J. Mol. Bio.*, 3:208–218 (1961) which is incorporated by reference herein. The G+C content was determined using the buoyant density procedure described by Schildkraut, et al., *J. Molec. Biol.*, 4:430–443 (1962) which is incorporated by reference herein.

III. RESULTS

A. Numbers and Kinds of Bacteria

Direct microscopic observations of rumen fluid from the two sheep fed the molasses diet showed a very large proportion of relatively large, nonmotile, gram-positive bacteria many of which showed club shapes and branching.

The MPN methanol cultures inoculated with rumen fluid from these sheep showed a predominance of similar bacteria and gave an MPN of $1.1 \times 10^9$ and $1.5 \times 10^8$ bacteria per ml of rumen fluid. Methane, even in tubes containing a large inocula, was never found in more than trace amounts while qualitative analysis of the culture supernatant indicated large amounts of acetic acid (as acetate) and butyric acid (as butyrate) but very little propionic acid (as propionate) were produced from methanol. Maximum growth occurred within ten days in all cultures showing growth, including those cultures which received the most dilute inoculum.

The MPN methanol cultures of sewage sludge gave similar results, except that number were lower ($9.5 \times 10^4$ bacteria per ml), and some of the cultures receiving more dilute inocula did not reach maximum growth until 11 days of incubation.

B. Isolation and Some Features of the Lower Aliphatic Carboxylic Acid-producing Bacteria MPN methanol cultures inoculated with the smallest amount of sheep rumen fluid and sewage sludge were diluted and used to inoculate methanol medium agar roll tubes. After 6 days of incubation, well-isolated colonies were evident in tubes inoculated with the highest dilution. Most of the colonies were observed to be the methanol-utilizing rods. Surface colonies were off-white, opaque, entire and convex and were 1–2 mm in diameter. Deep colonies were lenticular. Colonies were stabbed into methanol agar medium slants and good growth was obtained after 2 days of incubation. Microscopic examination revealed nonmotile, regularly shaped, cylindrical cells with rounded ends (average cell size, 1.2 mm×313 mm) that occurred mainly as single cells. After four to five days of incubation cells became more pleomorphic forming elongated cells that often showed knobs, which were usually centrally located, and branching forms. The colony and cellular morphology of isolates from the sheep rumen or sewage sludge were identical except that the rumen isolates tended to become more pleomorphic than the sewage isolates. All isolates were gram positive. A culture from sheep rumen (strain RF) and one from sewage sludge (strain S) were observed to be identical in all other characteristics.

Both strains were anaerobic. They failed to grow above the line of oxidation of resazurin in methanol agar, and did not grow in glucose medium prepared and incubated aerobically.

The optimum temperature for most rapid growth in methanol medium was 39° C. and the temperature range for growth was 17° C. to 47° C.

C. Heat resistance and spore formation

Some of the methanol-grown cultures survived exposure to 70° C. for 10 minutes, but none survived 80° C. for 15 minutes. All cultures grown in the Duncan and Strong sporulation medium survived 70° C. for 10 minutes, but only a third survived 80° C. for 15 minutes.

In no case were spores observed with the phase contrast microscope or in smears stained to detect spores.

D. Utilization of Substrate

Figure 1:
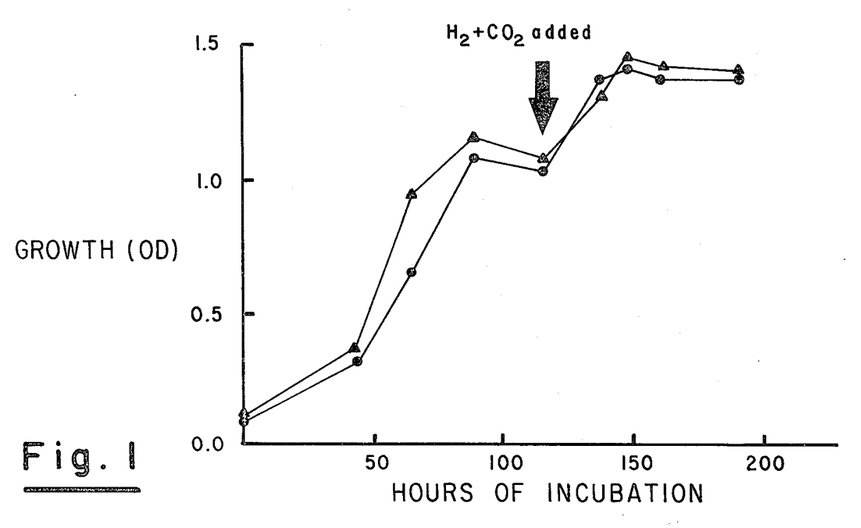
FIG. 1: Growth of *Eubacterium limosum* (strains RF and S) on 80% $H_2$—20% $CO_2$ medium (basal containing 5% rumen fluid). Arrow indicates repressurizing cultures to 2 atmospheres of 80% $H_2$—20% $CO_2$. Each point is the mean of triplicate tubes. Symbols: ●, strain RF; ▲, SI.

All four strains of *Eubacterium limosum* grew with $H_2$—$CO_2$ as the energy source, although strains RF and S grew much better than strains ATCC 8486 and L34. After inoculating the $H_2$—$CO_2$ medium with a methanol-grown culture of strains RF and S, 270 hours of incubation elapsed before growth was evident; however, growth was relatively good once it had started. Subsequent transfers into fresh $H_2$—$CO_2$ medium resulted in more rapid initiation of growth (FIG. 1). Cultures of strains ATCC 8486 and L34 reached OD's of approximately 0.2 in this medium. When growth stopped due to lack of $H_2$, it could be restarted by adding more $H_2$—$CO_2$ to the culture. Growth did not occur if $H_2$—$CO_2$ was replaced with 80% $N_2$—20% $CO_2$.

The generation time of strain RF at 39° C. in basal medium (5% rumen fluid) was 7 hours for $H_2$/$CO_2$ (50% $H_2$, 20% $CO_2$ and 30% $H_2$).

In the chemically defined $H_2$—$CO_2$ medium, 87.8 mM acetate and 2.75 mM butyrate were detected when strain RF was grown to maximum.

The fermentation balance for strain RF in a nutrient medium containing CO at different levels is given in Table I as follows:

TABLE I

Fermentation balance of *Eubacterum limosum* strain RF in basal medium containing two concentrations of $CO^a$.

| | mmol/liter$^b$ | |
|---|---|---|
| | 20% CO | 40% CO |
| Substrate utilized | | |
| CO | 58.0 | 120.2 |
| Fermentation products | | |
| Acetate | 12.6 | 24.3 |
| $CO_2$ | 23.9 | 57.0 |
| Recovery (%) | | |
| Carbon | 84.5 | 87.8 |
| Hydrogen | 86.8 | 80.7 |

$^a$Values are the mean of triplicate cultures incubated until maximum absorbance was reached.
$^b$Corrected for concentrations in uninoculated medium.

CO was added via sterile syringe to the desired percent based on 2 atmospheres (202 KPa) followed by pressurizing to 2 atmospheres with $N_2$. Initial percent CO was determined on duplicate medium blanks.

Since optimum production of aliphatic carboxylic acid has been observed to occur within the pH range of from about 7–7.2, it is generally necessary to provide a buffer to maintain this range. In such event, the produced acid(s) will be recovered as the salt(s). However, it is also possible to remove the acid(s) upon formation employing known and conventional procedures thereby maintaining the optimum pH level without the need for a buffer. Thus, for example, the acid(s) can be removed by operating the conversion process under vacuum and removing the volatile acid vapor(s) by condensation.

E. Nutritional Requirements

Figure 2:
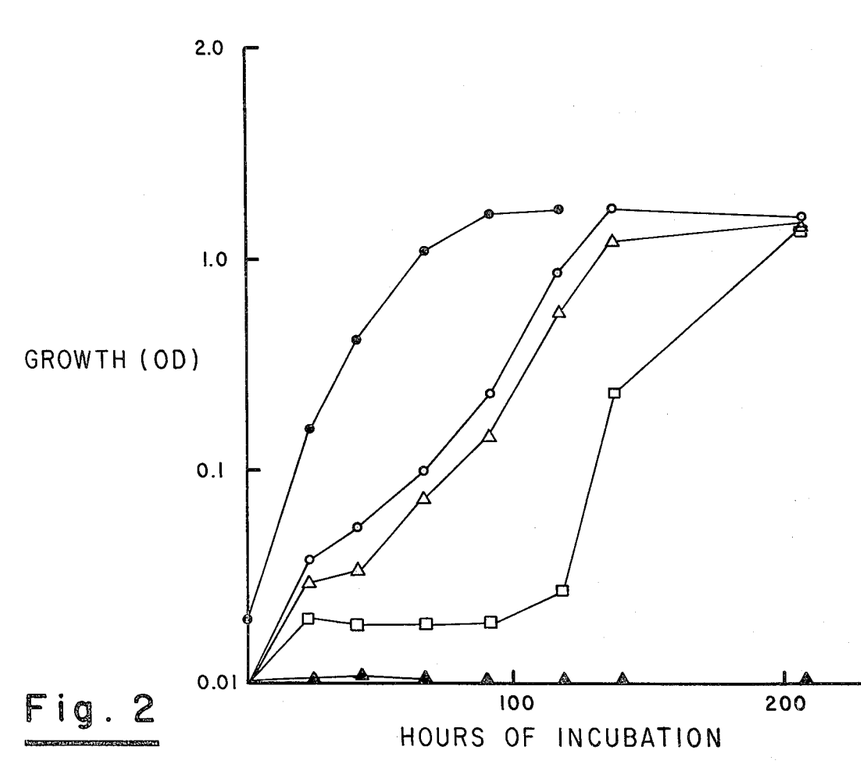
FIG. 2: Rumen fluid requirement by *Eubacterium limosum* (strain S) for growth in methanol (0.3%) medium replaced by sodium acetate resulting in a chemically defined methanol medium. Each point is the mean of triplicate tubes. Symbols: ●, 5% rumen fluid; O, 0.3% sodium acetate; Δ, 0.1% sodium acetate; □, 0.01% sodium acetate; ▲, no additions.

Strain S did not grow in methanol medium lacking rumen fluid, but the addition of sodium acetate (chemically defined medium) restored growth (FIG. 2). Sodium propionate could not replace the rumen fluid requirement. The lag phase in the chemically defined medium was increased as compared to the rumen fluid based medium but higher levels of acetate shortened the lag phase. The generation time at all levels of acetate was approximately 9 hours. Acetate was also required for growth on lactate, valine and isoleucine and was stimulatory to growth on glucose. Similar results were obtained with strain RF, strain L34 and ATCC 8486.

In contrast to methanol, cultures grown on $H_2$—$CO_2$ could be maintained without rumen fluid or sodium acetate. The doubling time did not increase in the absence of rumen fluid, but the lag phase lengthened.

Carbon dioxide was apparently required for utilization of methanol as growth did not occur in the methanol medium containing 100% $N_2$. Addition of sodium formate (0.2%) to this medium restored growth. $CO_2$ was observed to be stimulating to growth on CO.

Neither strain RF nor strain S grew in a chemically defined methanol medium if either biotin, Ca-D-pantothenate, or lipoic acid was deleted. The minimal vitamin requirements for growth on methanol were biotin, Ca-D-pantothenate and lipoic acid (TABLE II) as growth was normal for five passages through the methanol medium containing these three vitamins.

TABLE II

Growth response of *Eubacterium limosum* (strain RF) to the addition of vitamins to chemically defined methanol (0.2%) medium and a chemically defined $H_2$—$CO_2$ medium

| Conditions | Growth (OD)[a] | Days[c] |
|---|---|---|
| Methanol medium | | |
| no vitamins added | 0.05 | 11 |
| all vitamins added | 1.3 | 6 |
| biotin and pantothenate and lipoic acid[b] | 1.3 | 6 |
| $H_2$—$CO_2$ medium | | |
| no vitamins added | 0.06 | 17 |
| all vitamins added | 1.2 | 8 |
| biotin and pantothenate and lipoic acid[b] | 1.3 | 7 |

[a]Growth was the mean maximum value of triplicate tubes after five passages through the medium indicated. Growth did not occur in the absence of either biotin or pantothenate.
[b]Deletion of lipoic acid resulted in decreased growth rate and increased lag phase with each transfer (see text).
[c]Days required to reach maximum growth.

Cysteine was essential in the methanol medium as growth did not occur if it was deleted.

Figure 3:
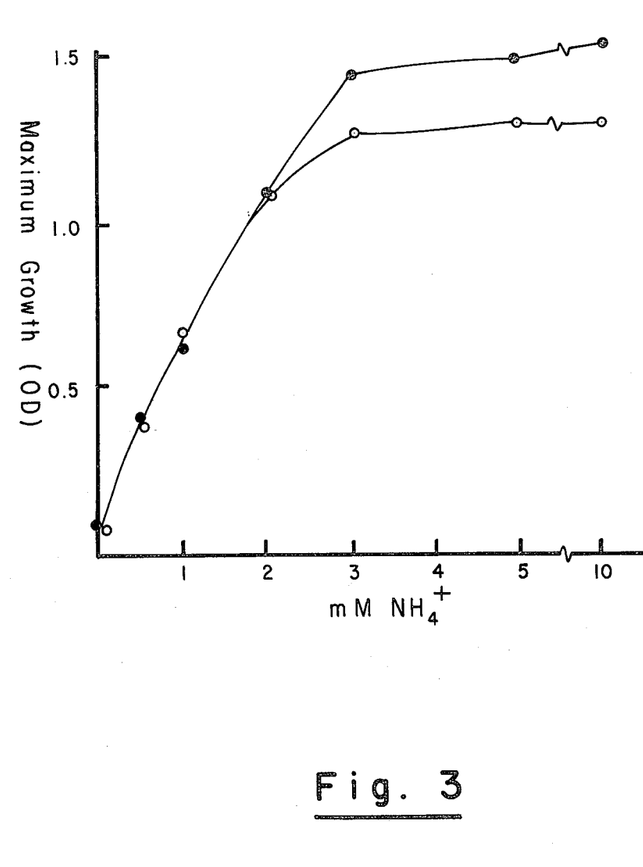
FIG. 3: Growth of *Eubacterium limosum* (strains RF and S) in chemically defined methanol medium (0.3% methanol, 0.3% sodium acetate.$3H_2O$) containing ammonium chloride as the sole nitrogen source. Each point is the mean maximum value of triplicate tubes. Symbols: ●, strain S; O, strain RF.
Figure 4:
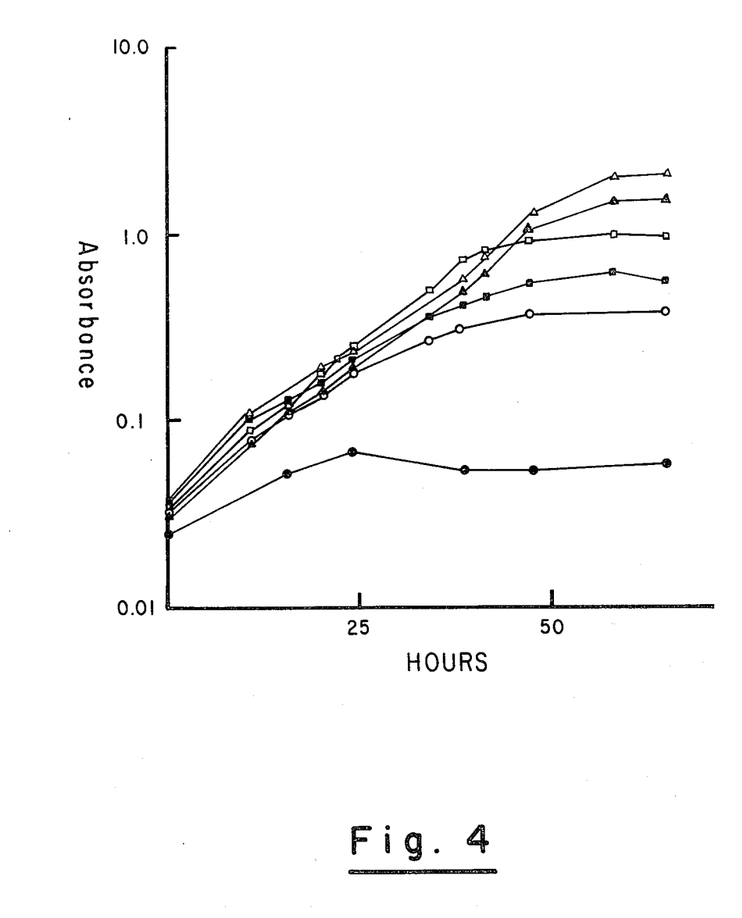
FIG. 4: Effect of increasing concentration of CO on the growth of *Eubacterium limosum* strain RF in basal medium with a gas phase containing 20% $CO_2$, CO as the energy source, and $N_2$ as the balance. CO was added via sterile syringe after which tubes were pressurized to 2 atmospheres with $N_2$. Percent CO is based on 2 atmospheres, and was determined in duplicate medium blanks. Tubes were inoculated with 0.1 ml of a $H_2$—$CO_2$ adapted culture grown to maximum $A_{600}$. Each point is the mean value of triplicate cultures. Symbols are: ●, 0%; O, 5%; ■, 10%; □, 20%; ▲, 30%; Δ, 40%.
Figure 5:
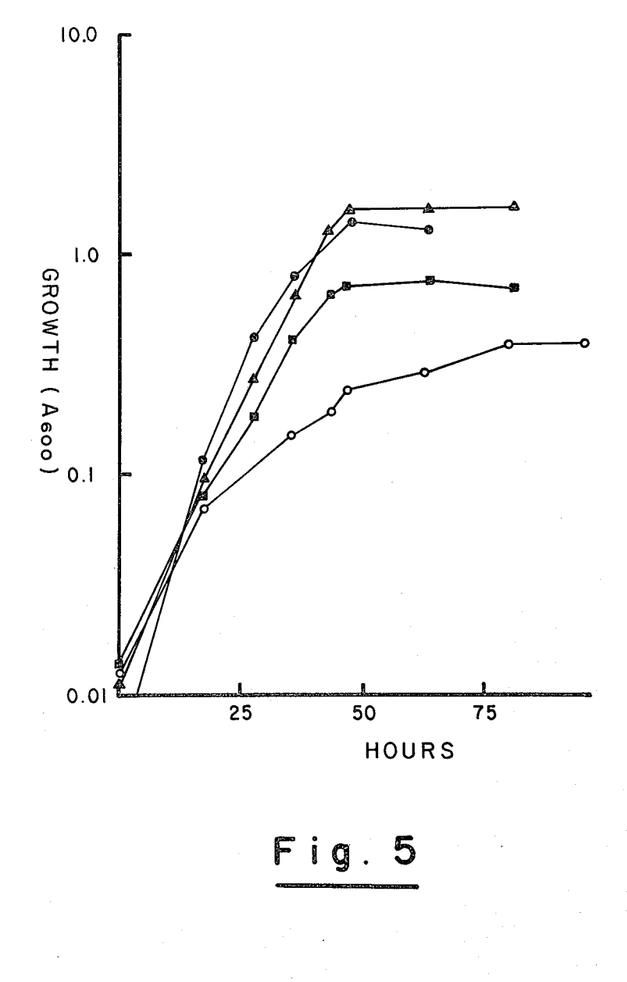
FIG. 5: Effect of increasing CO concentration to 50% and above on the ability of *Eubacterium limosum* strain RF to grow (39° C.) in a basal medium with 20% $CO_2$ and the balance $N_2$. Below 50% CO, tubes were prepared by adding CO via sterile syringe and pressurizing to 2 atmospheres (202 KPa) with $N_2$. 50%, 57% and 75% CO was added by pressurizing tubes with 100% CO to 2.0; 2.07 and 2.25 atmospheres, respectively. Percent CO is based on 2 atmospheres, and was determined in duplicate medium blanks for all CO concentrations. Tubes were inoculated with 0.05 ml of a $H_2$—$CO_2$ adapted culture grown to maximum $A_{600}$ in 50% CO prior to use as inoculum. Each point is the mean value of triplicate cultures. Symbols are: ●, 20%; ▲, 50%; ■, 57%; O, 75%.
Figure 6:
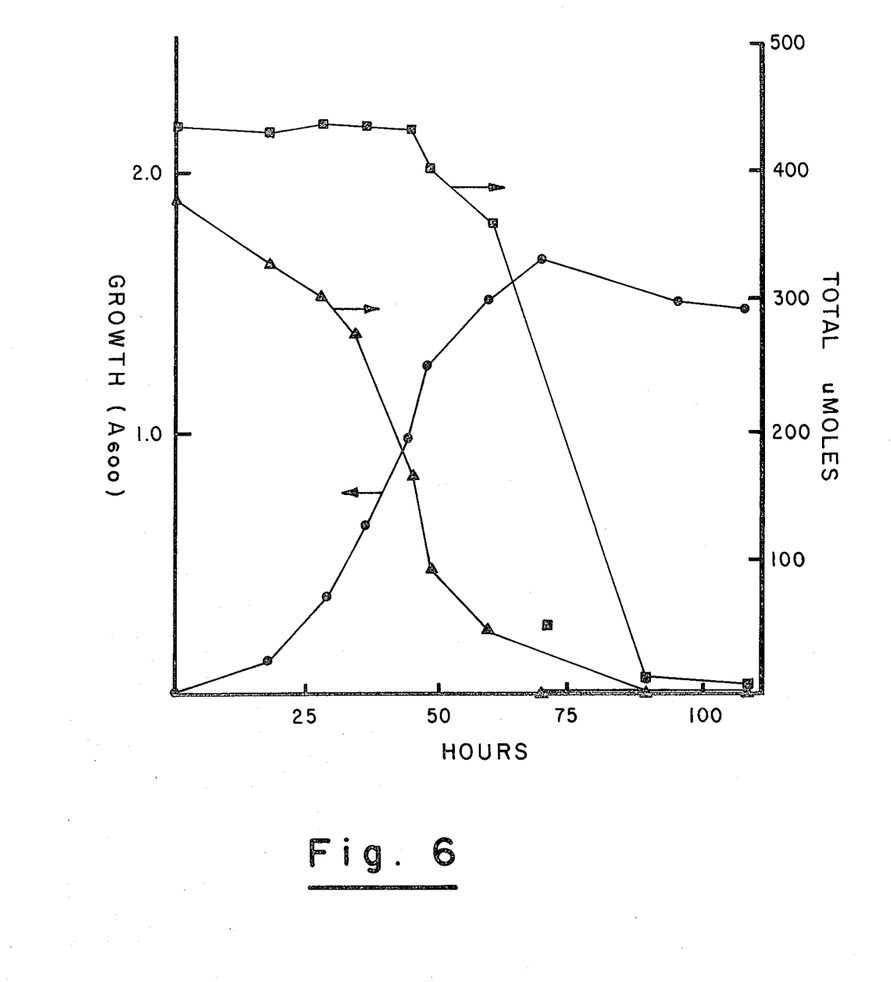
FIG. 6: Effect of carbon monoxide on the utilization of hydrogen by *Eubacterium limosum* strain RF during growth. Cultures were prepared by pressurizing basal medium to 1.5 atmospheres with $H_2$, then adding CO to 2 atmospheres (202 KPa). Initial CO concentration was determined on duplicate medium blanks. Symbols are: ●, growth ($A_{600}$); ▲, CO; ■, $H_2$.

The growth response of *Eubacterium limosum* to $NH_4Cl$ as nitrogen source in chemically defined methanol medium (FIG. 3) showed strain S reached higher maximum growth than strain RF, perhaps due to the difference in cellular morphology noted above. Maximum growth was observed at 5.0 mM $NH_4Cl$.

Only a few other nitrogen sources supported the growth of *Eubacterium limosum* (strain RF) as well as $NH_4Cl$ (TABLE III). These included casamino acids, cysteine, casitone, isoleucine and valine. Arginine, aspartic acid, glutamic acid, tyrosine and leucine were good nitrogen sources while other compounds tested were either poor nitrogen sources, or did not support growth. Results obtained with strain S were similar.

TABLE III

Growth response of *E. limosum* (strain RF) to various nitrogen sources in chemically defined methanol (0.2%) medium.[a]

| Nitrogen source[b] | Growth (OD)[c] | Days[d] |
|---|---|---|
| Casamino acids | 1.52 | 5.0 |
| Valine | 1.48 | 5.0 |
| Cysteine | 1.40 | 8.9 |
| Isoleucine | 1.35 | 8.1 |
| Casitone | 1.30 | 5.0 |
| Glutamic acid | 1.26 | 8.1 |
| Arginine | 1.22 | 7.2 |
| Aspartic acid | 1.16 | 6.0 |
| Tyrosine | 1.16 | 7.1 |
| Leucine | 1.13 | 6.6 |
| Histidine | 1.05 | 6.0 |
| Serine | 1.05 | 6.6 |
| Methionine | 1.03 | 8.1 |

TABLE III-continued

Growth response of *E. limosum* (strain RF) to various nitrogen sources in chemically defined methanol (0.2%) medium.[a]

| Nitrogen source[b] | Growth (OD)[c] | Days[d] |
|---|---|---|
| Phenylalanine | 0.97 | 8.9 |
| Tryptophan | 0.87 | 9.4 |
| Threonine | 0.75 | 9.4 |
| Basal | | |
| 1.0 mM $NH_4Cl$ | 0.66 | 5.0 |
| 3.0 mM $NH_4Cl$ | 1.27 | 6.0 |

[a]Medium contained 1.0 mM $NH_4Cl$ and 2.0 mM of nitrogen source being tested.
[b]All nitrogen sources were added before autoclaving except urea, biuret, and allantoin which were filter-sterilized and added to cooled sterile medium. Those nitrogen sources which were negative included adenine, alanine, allantoin, biuret, cytosine, glycine, lysine, proline, thymine, and urea.
[c]Growth was measured as OD and was the mean maximum value of triplicate tubes.
[d]Time-required to reach maximum growth.

F. G+C determination

The buoyant density of the DNA isolated from strain RF grown on methanol was 1.708 g $cm^{-3}$, and the calculated G+C content was 49.0 mol%.

In the attached figures of drawing, the following symbols having the indicated meanings were employed.

What is claimed is:

1. A process for preparing a lower aliphatic carboxylic acid of from 1 to 6 carbon atoms and/or a salt thereof which comprises culturing *Eubacterium limosum* in a nutrient medium containing at least one member of the group consisting of carbon monoxide and a mixture of hydrogen and carbon oxide under substantially anaerobic conditions.

2. The process of claim 1 wherein the microorganism is *Eubacterium limosum*, strain RF or S.

3. The process of claim 1 wherein the lower aliphatic carboxylic acid is acetic acid, valeric acid, butyric acid, caproic acid or a metal salt thereof.

4. The process of claim 1 wherein the salt is an alkali metal or alkaline earth metal salt.

5. The process of claim 1 wherein the carbon oxide is carbon monoxide, carbon dioxide or mixtures thereof.

6. The process of claim 1 wherein the mixture of hydrogen and carbon oxide is obtained from the gasification of a carbon-containing material.

7. The process of claim 6 wherein the carbon-containing material is coal.

8. The process of claim 1 wherein the nutrient medium contains a utilizable source of nitrogen.

9. The process of claim 1 wherein the nutrient medium contains at least one vitamin for promoting growth of the microorganism.

10. The process of claim 1 wherein the hydrogen:carbon oxide volume ratio is from about 0.2:1 to about 10:1.

11. The process of claim 1 wherein the hydrogen:carbon oxide volume ratio is from about 0.4:1 to about 5:1.

12. The process of claim 1 wherein *Eubacterium limosum* is propagated in a methanol-containing nutrient medium under anaerobic conditions and the microorganism is thereafter transferred to a nutrient medium containing at least one member of the group consisting of carbon monoxide and a mixture of hydrogen and a carbon oxide.

* * * * *

UNITED STATES PATENT AND TRADEMARK OFFICE
CERTIFICATE OF CORRECTION

PATENT NO. : 4,377,638
DATED : Mar. 22, 1983
INVENTOR(S) : Marvin P. Bryant; Barbara R. S. Genthner It is certified that error appears in the above—identified patent and that said Letters Patent is hereby corrected as shown below:

Column 8, line 16, "$H_2$" should read -- $N_2$ -- .

Signed and Sealed this

Twenty-eighth Day of June 1983

[SEAL]

Attest:

GERALD J. MOSSINGHOFF

Attesting Officer    Commissioner of Patents and Trademarks